(12) United States Patent
Kim et al.

(10) Patent No.: US 9,987,339 B2
(45) Date of Patent: Jun. 5, 2018

(54) PHARMACEUTICAL COMPOSITION WITH IMPROVED STABILITY CONTAINING FACTOR VII FUSION PROTEIN

(71) Applicant: TIUMBIO CO., LTD., Gyeonggi-do (KR)

(72) Inventors: Hong-Kee Kim, Gyeonggi-do (KR); Ho Chul Shin, Gyeonggi-do (KR); Yoon-Jung Lee, Gyeonggi-do (KR); Ho Soon Lee, Gyeonggi-do (KR); Ji-Hye Lee, Seoul (KR); Seok-chan Kang, Gyeonggi-do (KR); Hun-Taek Kim, Seoul (KR)

(73) Assignee: TIUMBIO CO., LTD., Gyeonggi-Do (KR)

( * ) Notice: Subject to any disclaimer, the term of this patent is extended or adjusted under 35 U.S.C. 154(b) by 0 days. days.

(21) Appl. No.: 15/105,434

(22) PCT Filed: Dec. 16, 2014

(86) PCT No.: PCT/KR2014/012403
§ 371 (c)(1),
(2) Date: Jun. 16, 2016

(87) PCT Pub. No.: WO2015/093819
PCT Pub. Date: Jun. 25, 2015

(65) Prior Publication Data
US 2017/0000861 A1    Jan. 5, 2017

(30) Foreign Application Priority Data
Dec. 16, 2013 (KR) .................. 10-2013-0156740

(51) Int. Cl.
| | |
|---|---|
| *C12N 9/96* | (2006.01) |
| *A61K 38/48* | (2006.01) |
| *A61K 38/40* | (2006.01) |
| *A61K 38/46* | (2006.01) |
| *A61K 47/02* | (2006.01) |
| *A61K 47/10* | (2017.01) |
| *A61K 47/18* | (2017.01) |
| *A61K 47/26* | (2006.01) |
| *C07K 14/79* | (2006.01) |
| *C07K 14/81* | (2006.01) |

(52) U.S. Cl.
CPC .......... *A61K 38/4846* (2013.01); *A61K 38/40* (2013.01); *A61K 38/46* (2013.01); *A61K 47/02* (2013.01); *A61K 47/10* (2013.01); *A61K 47/183* (2013.01); *A61K 47/26* (2013.01); *C07K 14/79* (2013.01); *C07K 14/811* (2013.01); *C07K 2319/35* (2013.01); *C07K 2319/70* (2013.01); *C12Y 304/21021* (2013.01)

(58) Field of Classification Search
None
See application file for complete search history.

(56) References Cited

U.S. PATENT DOCUMENTS

| | | | |
|---|---|---|---|
| 8,372,800 B2 | 2/2013 | Besman et al. | ................. 514/1.1 |
| 2006/0130158 A1 | 6/2006 | Turner et al. | ..................... 800/7 |
| 2013/0116410 A1 | 5/2013 | Ivarsson et al. | ............... 530/351 |

FOREIGN PATENT DOCUMENTS

| | | | |
|---|---|---|---|
| KR | 10-1331101 | 11/2013 | |
| WO | WO 00/48635 A1 | 8/2000 | ............. A61K 47/10 |
| WO | WO 2008/078189 A2 | 7/2008 | ............... A61K 9/19 |
| WO | WO 2010-148253 | 12/2010 | |
| WO | WO 2011-152694 | 12/2011 | |

OTHER PUBLICATIONS

Qiang et al. (Pharm. Rev., vol. 54, No. 4, 2002, pp. 561-587).*
International Search Report (ISR) dated Mar. 20, 2015 in PCT/KR2014/012403 published as WO 2015/093819 with English Translation.
Carpenter, J.F. et al., (2002). "Rationale design of stable lyophilized protein formulations: theory and practice", in *Rationale Design of Stable Protein Formulations-Theory and Practice*.
Nedergaard, H. et al., (2008). "In vitro stability of lyophilized and reconstituted recombinant activated FVII formulated for storage at room temperature", *Clinical Therapeutics*, 30(7):1309-1315.
Extended European Search Report from corresponding European Patent Application No. 14871697.0 dated Jun. 14, 2017.

* cited by examiner

*Primary Examiner* — Hope Robinson
(74) *Attorney, Agent, or Firm* — Harness, Dickey & Pierce, P.L.C.

(57) ABSTRACT

The present invention provides a pharmaceutical composition with improved stability, comprising a fusion protein comprising Factor VII (FVII) and transferrin, as an active ingredient, wherein the transferrin is linked to the C-terminus of the FVII; and trehalose or glycine as a bulking agent. The composition can store FVII and a variant thereof stably at room temperature for a long period of time. Thus it can be used as a useful therapeutic agent for patients suffering from hemophilia or congenital FVII deficiency.

16 Claims, 2 Drawing Sheets

PHARMACEUTICAL COMPOSITION WITH IMPROVED STABILITY CONTAINING FACTOR VII FUSION PROTEIN

CROSS-REFERENCE TO RELATED APPLICATIONS

This application is a national phase application of PCT Application No. PCT/KR2014/012403, filed on Dec. 16, 2014, which claims the benefit and priority of Korean Patent Application No. 10-2013-0156740, filed Dec. 16, 2013. The entire disclosures of the applications identified in this paragraph are incorporated herein by reference.

FIELD

The present invention relates to a pharmaceutical composition with improved stability, containing a fusion protein of factor VII (FVII), and more particularly, it relates to a pharmaceutical composition with improved stability, containing a fusion protein of FVII and transferrin, as an active ingredient, and trehalose or glycine as a bulking agent.

BACKGROUND

Blood coagulation phenomenon includes a series of enzymatic reactions in which coagulation factors are involved, and many of the coagulation factors are proteases which contain serine at the active site. Activated FVII, also called proconvertin, is one of the above factors, which has a molecular weight of about 50 kDa, and it is involved in the blood coagulation mechanism. It is a glycoprotein of serine protease family, and the synthesis of its active form depend on vitamin K.

Activated FVII operates locally in the presence of tissue factors released after tissue injury which causes bleeding (haemorrhage), even in the absence of factor VIII or factor IX. For this reason, factor VII, preferably its activated form, has been used for a long time for the treatment of specific blood coagulation disorders which are manifested by bleeding.

Currently, medications for the treatment of patients suffering from hemophilia or congenital FVII deficiency are commercially available. NovoSeven® produced by NovoNordisk has been approved in the European market since 1996, and it was approved in the US market in 1999. NovoSeven® is a medication whose active ingredient is eptacog alpha (human recombinant activated coagulation FVII produced from BHK baby hamster kidney cells by genetic engineering). The medication also contains sodium chloride (2.92 g/L), calcium chloride dihydrate (1.47 g/L), glycylglycine (1.32 g/L), polysorbate 80 (0.07 g/L) and mannitol (30 g/L).

Also, there is a variant of NovoSeven (called NovoSeven® RT), which can be stored at room temperature (25° C.). This second product is composed of sodium chloride (2.92 g/L), calcium chloride dihydrate (1.47 g/L), glycylglycine (1.32 g/L), polysorbate 80 (0.07 g/L), mannitol (25 g/L) and hydrochloric acid and sodium hydroxide to adjust the pH, and it also contains sucrose (10 g/L) and methionine (0.5 g/L) (used as an antioxidant). To return this product to a solution, water for injection and histidine are required. NovoSeven® RT was approved in the European and US markets in 2008.

An article published in 2008 by Nedergaard and his colleagues [Nedergaard H. et al., In vitro stability of lyophilized and reconstituted recombinant activated FVII formulated for storage at room temperature, Clinical Therapeutics, Vol 30, No. 7, p 1309-1315, 2008] reported that NovoSeven® RT could be stably maintained in its lyophilized form for 24 months at 25° C., for 12 months at 30° C., for 6 months at 40° C., and for 12 hours at 50° C. and 60° C. Also, this products was stable for only 6 hours after liquid reconstitution, and thus, it is recommended to inject such product within 3 hours after the reconstitution.

Meanwhile, it has been reported that the half-life of FVII in plasma is about 4 hours (3-6 hours), while that of FVIIa is about 2.5 hours. Due to the short half-life, FVIIa is required to be administered via multiple intravenous injections or continuous injection for the hemostasis. However, this would seriously limit the therapeutic uses of FVIIa in terms of high treatment expenses and the patient's discomfort. To overcome these problems, methods have been provided for preparing fusion proteins comprising FVII and a fusion partner linked thereto, but the resulting proteins had a problem of losing their biological activities, even though the short in-vivo half-life was somewhat improved compared to the unfused protein. Accordingly, the present inventors have developed a fusion protein in which transferrin is linked to the C-terminus of FVII, and showed that this fusion protein retains high biological activity of the FVII while exhibiting increased in-vivo half-life compared to the natural FVII (see Korean Patent No. 10-1331101).

However, the above fusion protein has been found to show significantly reduced stability when it is formulated in a conventionally known composition (e.g., NovoSeven® RT formulation). Therefore, there is a need to develop a composition which has excellent stability, is easy to handle, and can be conveniently used for the patients suffering from hemophilia or congenital FVII deficiency.

SUMMARY OF THE INVENTION

Therefore, it is an object of the present invention to provide a pharmaceutical composition with improved stability, containing a fusion protein of FVII.

In accordance with one object of the present invention, there is provided a pharmaceutical composition with improved stability, comprising a fusion protein comprising FVII and transferrin, as an active ingredient, wherein the transferrin is linked to the C-terminus of the factor VII; and trehalose or glycine as a bulking agent.

As a pharmaceutical composition according to the present invention contains glycine or trehalose as a bulking agent unlike other conventional formulations, the fusion protein of FVII can be stored stably at room temperature for a long period of time. Thus, it can be used as a useful therapeutic agent for the patients suffering from hemophilia or congenital FVII deficiency.

DETAILED DESCRIPTION OF THE INVENTION

Figure 1:
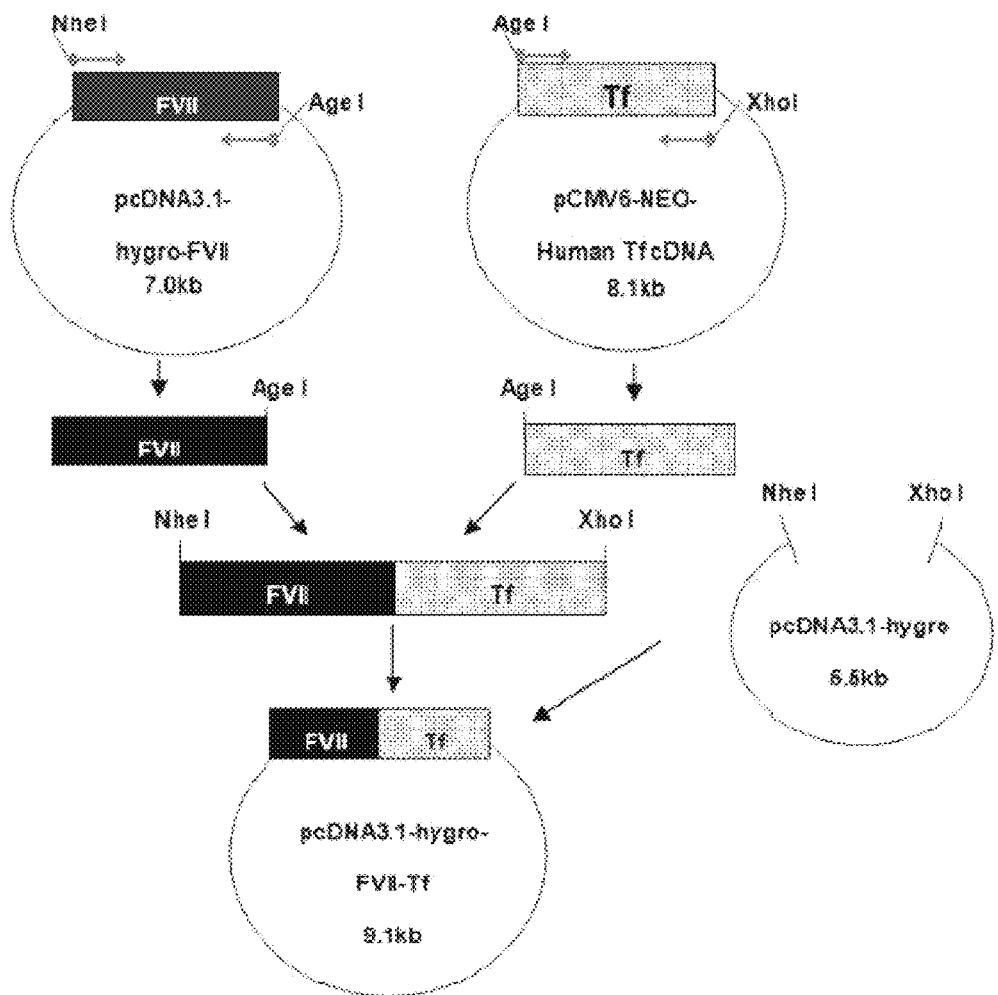
FIG. 1 is a schematic diagram showing a process for preparing the FVII-Tf expression vector from a vector containing a cDNA encoding FVII and a vector containing a cDNA encoding transferrin (Tf).

The present invention provides a pharmaceutical composition with improved stability, comprising a fusion protein comprising FVII and transferrin, as an active ingredient, wherein the transferrin is linked to the C-terminus of the factor VII; and trehalose or glycine as a bulking agent.

In a pharmaceutical composition of the present invention, FVII fusion protein can be stored stably at room temperature for a long period of time without reduction of the activity of the FVII fusion protein. As used herein, the term "room temperature" refers generally to a room temperature between 10° C. and 30° C., preferably, between 15° C. and 25° C. Specifically, a pharmaceutical composition of the present invention can significantly reduce the amount of high molecular weight (HMW) aggregates formed during the process of lyophilization or storage. The pharmaceutical compositions of the present invention may be present in a lyophilized or liquid state, preferably in a lyophilized state.

The fusion protein of FVII as used herein is a fusion protein comprising FVII and transferrin, and transferrin is linked to the C-terminus of FVII. A fusion protein linked in the order of FVII-transferrin shows superior effect as a therapeutic agent as compared to a fusion protein linked in the order of tranferrin-FVII, due to the exposure of the N-terminus of FVII.

The FVII and transferrin of the above fusion protein may be derived from any mammal, preferably human FVII and human transferrin. More preferably, the FVII and transferrin may have at least 95% of sequence homology with those of natural proteins found in human blood, respectively. Most preferably, FVII has the amino acid sequence of SEQ ID NO: 1, and transferrin has the amino acid sequence of SEQ ID NO: 2.

In addition, the above fusion protein may encompass a functional equivalent or derivative which has a substantially equivalent functional activity. Exemplary functional equivalents include variants prepared by deletion, insertion or non-conservative or conservative substitution of any amino acid residue, or a combination thereof in the amino acid sequences represented by SEQ ID NOs: 1 and 2, respectively, in which such changes do not substantially alter active sites or domains offering biological activities to FVII.

In some cases, the fusion protein may be modified, e.g., by phosphorylation, sulfation, acrylation, glycosylation, methylation, farnesylation, acetylation, amidation, etc., for the increase or reduction of its physical or chemical properties, and such functional derivatives also fall within the scope of the present invention so long as the activity of FVII is substantially retained by such modification.

A fusion protein of the present invention may further contain recognition sequence(s) for a restriction enzyme between FVII and transferrin in order to facilitate the insertion of a linker described below. The restriction enzyme recognition sequence may be any sequence known in the art, and Agel recognition sequence (A/CCGGT) may be preferably used. In other words, fusion proteins, in which a restriction enzyme recognition sequence is linked to the C-terminus of FVII and transferrin is linked to such restriction enzyme recognition sequence, are included within the scope of the present invention.

A fusion protein of the present invention may contain a linker between FVII and transferrin. The linker may have 1 to 100 amino acids, preferably 1 to 75 amino acids, more preferably 5 to 25 amino acids, and it may be any peptides which can separate FVII and transferrin. A linker may have a stable secondary structure such as a helix or be may originated from IgG hinge region.

Preferably, a linker may rotate freely in an aqueous solution and does not have a fixed structure, and, therefore, it would be non-immunogenic and would increase FVII activities of fusion proteins by minimizing the potential interference between two fusion partners. Further, such a flexible linker may contain glycine (G) and serine (S) in a repeated or random pattern. For example, a linker may comprise $(GGGGS)_N$ wherein N is an integer ranging from 1 to 20 (SEQ ID NOs: 5-24). In addition, amino acid sequences having at least 80% of homology with the above linker, preferably having at least 85%, may also be used as a linker for a fusion protein of the present invention.

More information on the fusion protein can be found in Korean Patent No. 10-1331101.

As used herein, the term "composition with improved stability" or "stable composition" refers to the minimization of aggregate (insoluble or soluble) formation to maintain the biological activity and stability of the protein during the production or storage of a composition of the present invention, and/or reduction of chemical degradation or maintenance of pH without substantial modification of the protein. In case of lyophilization of the composition, the stabilization of the composition encompasses lyoprotection and cryoprotection of the protein.

"Physical stability" of the FVII fusion protein refers to reduction or absence of the formation of dimeric, oligomeric or polymeric aggregates (insoluble or soluble) of factor VII, and reduction or absence of the arbitrary structural modification of molecules.

The term "chemical stability" refers to the absence or reduction of any chemical modification of the FVII fusion protein under the accelerated conditions during storage. For example, hydrolysis, de-amination and/or oxidation phenomena are prevented or delayed. In addition, the oxidation of a sulfur-containing amino acid is limited.

Hereinafter, the ingredients used in a composition of the present invention are described in detail.

The composition of the present invention comprises as an active ingredient, a fusion protein comprising FVII and transferrin. The FVII fusion protein is described above. The FVII fusion protein can be comprised in an amount of 0.1 to 1000 mg/ml, preferably 0.1 to 100 mg/ml, more preferably 0.2 to 50 mg/ml, most preferably 0.2 to 10 mg/ml based on the total weight of the composition, but is not limited thereto.

A composition of the present invention comprises trehalose or glycine as a bulking agent. A composition of the present invention does not comprise a polyol as a bulking agent, but contains trehalose or glycine instead of a polyol, whereas the conventional NovoSeven® RT of NovoNordisk comprises mannitol, a polyol, as a bulking agent. An example of polyol which is not used in the present invention is mannitol.

According to the experimental result of the present invention, a formulation employing trehalose or glycine shows significantly higher storage stability as compared to a formulation using mannitol as a bulking agent.

As a bulking agent, trehalose can be comprised in an amount of 0.1 to 20 weight % based on the total weight of the composition, and glycine can be comprised in an amount of 0.1 to 20 weight % based on the total weight of the composition, but not limited thereto.

In one embodiment, a pharmaceutical composition of the present invention further comprises polysorbate 20 or poloxamer 188 as a surfactant.

While the conventional NovoSeven® RT of NovoNordisk comprises polysorbate 80 as a surfactant, a composition of the present invention comprises polysorbate 20 or poloxamer 188 as a surfactant instead of polysorbate 80.

According to the experimental result of the present invention, a formulation employing polysorbate 20 or poloxamer 188 shows significantly higher storage stability as compared to a formulation using polysorbate 80 as a surfactant.

As a surfactant, polysorbate 20 can be comprised in an amount of 0.0005 to 2.5 weight % based on the total weight of the composition, and poloxamer 188 can be comprised in an amount of 0.05 to 2.5 weight % based on the total weight of the composition, but not limited thereto.

In one embodiment, a pharmaceutical composition of the present invention can further comprise, as a stabilizer, at least one selected from the group consisting of sodium chloride, calcium chloride, trehalose, sucrose and threonine. In another embodiment, a pharmaceutical composition of the present invention can further comprise L-histidine as a buffer. In another embodiment, a pharmaceutical composition of the present invention can further comprise methionine as an antioxidant.

The stabilizer described above plays a role of preventing the protein's unfolding during lyophilization, and trehalose or sucrose is frequently used conventionally [See Rationale design of stable lyophilized protein formulations: theory and practice, in Rationale Design of Stable Protein Formulations-Theory and Practice, 2002].

Particularly, trehalose used as a stabilizer can overlap with trehalose used as a bulking agent, but since the amount of trehalose used as a stabilizer is very small in the composition as compared to the trehalose used as a bulking agent, trehalose can also function as a stabilizer in a composition where trehalose is employed as a bulking agent but not as a stabilizer. On the other hand, trehalose cannot function as a bulking agent in a composition where trehalose is used as a stabilizer but not as a bulking agent.

In addition, according to the experimental result of the present invention, a composition employing 6% trehalose as a bulking agent showed cake formation during lyophilization, which supports that trehalose functioned as a bulking agent. Furthermore, a composition using glycine as a bulking agent (without trehalose) and trehalose as a stabilizer also showed cake formation, which supports that glycine used in large quantities functioned as a bulking agent and trehalose functioned as a stabilizer.

A composition of the present invention comprises, as a stabilizer, at least one selected from the group consisting of sodium chloride, calcium chloride, trehalose, sucrose and threonine, whereas the conventional NovoSeven® RT of NovoNordisk comprises all of the sodium chloride, calcium chloride dihydrate, sucrose and glycylglycine as stabilizers. In addition, no glycylglycine is contained in the composition of the present invention.

According to the experimental result of the present invention, a formulation comprising at least one selected from the group consisting of sodium chloride, calcium chloride, trehalose, sucrose and threonine as a stabilizer showed significantly higher storage stability as compared to a formulation comprising sodium chloride, calcium chloride dihydrate, sucrose and glycylglycine as stabilizers. The sodium chloride, calcium chloride, trehalose, sucrose and threonine can be comprised in the amounts of 0.01 to 20 weight %, 0.01 to 10 weight %, 0.1 to 10 weight %, 0.1 to 10 weight % and 0.1 to 45 weight based on the total weight of the composition, respectively.

L-histidine used as a buffer in the composition of the present invention can be used in an amount of 0.5 to 1000 mM based on the total weight of the composition, but is not limited thereto.

Methionine used as an antioxidant in the composition of the present invention can be used in an amount of 0.01 to 50 weight % based on the total weight of the composition, but is not limited thereto.

The composition of the present invention can be used for the treatment of hemophilia or congenital FVII deficiency, and an effective amount of injectable formulation is administered to the patients in need of such treatment.

The hemophilia may be of type A or B. Hemophilia A is caused by factor VIII deficiency, whereas hemophilia B is caused by factor IX deficiency. Congenital FVII deficiency is a rare hereditary haemorrhagic disease (autosomal recessive transmission) caused by the decrease or absence of coagulation FVII.

The injectable formulation can be administered parenterally, intravenously, subcutaneously, or intramuscularly in an amount accessed by a physician. It can be administered through any suitable routes and means.

Hereinafter, the present invention is described more specifically by the following examples, but the present invention is not limited thereto.

Preparation Example 1: Preparation of Fusion Protein of FVII and Transferrin

With reference to the method disclosed in Korean Patent No. 10-1331101, fusion proteins of FVII and transferrin were prepared as described below. In summary, after preparing a FVII-Tf expression vector, the vector was allowed to express in a cell line, followed by purification of a fusion protein FVII-Tf.

<1-1> Preparation of FVII plasmid vector (pcDNA3.1-hygro-FVII)

The RNA purified from Hep G2 cells (KCLB No. 88065) was used as a template for reverse transcription. Complementary DNA (cDNA) transcript was amplified by PCR using FVII gene specific primers, FVII-F and FVII-R (SEQ ID NOs: 3 and 4) to obtain an open reading frame (ORF) of human FVII gene. The ORF of FVII (FVII-ORF) was ligated to pcDNA3.1-hygro vector (Invitrogen). The ligated vector was verified by restriction digestion with ApaI, XbaI, EcoRI, NcoI and PstI, and DNA sequencing. This vector was designated as"pcDNA3.1-hygro-FVII".

<1-2> Preparation of FVII-Tf Expression Vector (pcDNA3.1-hycro-FVII-Tf)

FVII cDNA prepared in Example 1 was linked to human transferrin (Tf) cDNA in order to be expressed as a single zymogen in an animal cell. Human tranferrin cDNA was purchased from Origene (Cat #: SC322130), to secure a cDNA having a sequence identical to the GenBank Accession No.: NM_001063.2. The fusion protein would have the following structure: (leader peptide)-(mature FVII)-(Thr-Gly)-(mature Tf) (the leader peptide consists of a signal peptide (prepeptide) not present in mature FVII and a propeptide to be cleaved by a processing enzyme, which is composed of 38 amino acids and corresponds to amino acids 1 to 38 in the amino acid sequence of SEQ ID NO: 1).

A cloning strategy for linking FVII cDNA and Tf cDNA is shown in FIG. 1. First, FVII cDNA was amplified from pcDNA3.1-hygro-FVII vector by PCR.

Next, Tf was amplified using human transferrin cDNA as a template.

The amplified FVII and Tf cDNAs were linked by a series of restriction digestion and ligation. Each DNA amplified by PCR was treated with a restriction enzyme, which was then purified and ligated. The ligated DNA was subcloned into pcDNA3.1-hygro vector (Invitrogen) treated with NheI/ShoI. The size and sequence of the insert was further verified by DNA sequencing.

<1-3> Preparation of FVII-Tf Fusion Protein

A culture solution was prepared by using a cell line which was transfected with FVII-Tf expression vector prepared in Example <1-2> through Bioreactor culture. A serum-free medium supplemented with glutamine (GIBCO, Cat No. 25030-081) and vitamin K (Daihan Pharm. Co.) was used as the preparation medium.

<1-4> Purification of FVII-Tf Fusion Protein

In order to eliminate the cells and cell debris remaining in the culture medium obtained from the spinner flask culture, the culture medium was filtered through 0.22 μm filter (corning). The filtered culture medium was subjected to ultrafiltration using tangential-flow membrane (satorious, 30 KDa), and concentrated. The concentrated medium was applied to the XK16/20 (GE healthcare) column filled with Q-sepharaose Fast Flow (GE healthcare, 17 0510-01) resin. Before applying the medium, the Q-sepharaose Fast Flow column was equilibrated with 5-fold column volume or more of an equilibration buffer (20 mM Tris, pH 8.0, 20 mM NaCl). After pouring the concentrated medium, 5-fold column volume or more of the equilibration buffer was poured to wash the impurities away. Then, after pouring 3-fold column volume of the washing buffer solution (20 mM Tris, pH 8.0, 191.5 mM NaCl) to eliminate the inactivated form of FVII-Tf, FVII-Tf fusion protein was eluted with elution buffer solution (20 mM Tris, pH 8.0, 1 M NaCl, 5 mM $CaCl_2$).

Examples 1 to 4: Preparation of Lyophilized Compositions Comprising Glycine or Trehalose as a Bulking Agent According to the composition of Table 1 below, the lyophilized compositions (pH 7) of Examples 1 to 4 comprising FVII-Tf fusion protein obtained in Preparation Example 1 and glycine or trehalose as a bulking agent were prepared.

Specifically, FVII-Tf fusion protein was put into a semi-permeable membrane (MWCO=10 KD), and was sufficiently dialyzed for 24 hours against the solutions according to the compositions described in Table 1 which contains glycine or trehalose as bulking agent. Temperature was maintained at the cold condition of 2~8° C. After the dialysis was completed, each formulation was filtration-sterilized by passing through a 0.2 μm filter. The formulations were put into glass vials in equal volumes and lyophilized.

TABLE 1

| | Ingredients | Example 1 | Example 2 | Example 3 | Example 4 |
|---|---|---|---|---|---|
| Active ingredient | FVII-Tf (mg/ml) | 1 | 1 | 1 | 1 |
| Bulking agent | Glycine (%) | 2 | 2 | 2.5 | — |
| | Trehalose (%) | — | — | — | 6 |
| Surfactant | Poloxamer 188 (%) | 0.1 | 0.1 | 0.1 | 0.1 |
| Buffer | L-histidine (mM) | 10 | 10 | 10 | 10 |
| Stabilizer | Sodium chloride (%) | 0.23 | — | 0.1 | 0.23 |
| | Calcium chloride (%) | — | 0.15 | 0.1 | 0.1 |
| | Trehalose (%) | — | — | 1 | — |
| | Sucrose (%) | 1 | 1 | — | — |
| Anti-oxidant | Methionine (%) | — | — | 0.05 | 0.05 |
| | pH | 7 | 7 | 7 | 7 |

Comparative Examples 1 to 4: Preparation of Lyophilized Compositions Comprising Mannitol as a Bulking Agent According to the composition of Table 2 below, the lyophilized compositions (pH 7) of Comparative Examples 1 to 4 comprising FVII-Tf fusion protein obtained in Preparation Example 1 and mannitol as a bulking agent were prepared. Specific preparation process is the same as the method described in Examples 1 to 4.

TABLE 2

| | Ingredients | Comparative Example 1 | Comparative Example 2 | Comparative Example 3 | Comparative Example 4 |
|---|---|---|---|---|---|
| Active ingredient | FVII-Tf (mg/ml) | 1 | 1 | 1 | 1 |
| Bulking agent | Mannitol (%) | 4 | 4 | 2.5 | 2.5 |
| Surfactant | Poloxamer 188 (%) | 0.1 | 0.1 | 0.1 | 0.1 |
| Buffer | L-histidine (mM) | 10 | 10 | 10 | 10 |
| Stabilizer | Sodium chloride (%) | 0.23 | — | 0.5 | 0.23 |
| | Calcium chloride (%) | — | 0.15 | 0.1 | 0.1 |
| | Trehalose (%) | — | — | 1 | 1 |
| | Sucrose (%) | 1 | 1 | — | — |
| Anti-oxidant | Methionine (%) | — | — | 0.05 | 0.05 |
| | pH | 7 | 7 | 7 | 7 |

Experimental Example 1: Analysis of Stability of Compositions According to Type of Bulking Agent <1-1> Analysis of the Amount of High Molecular Weight Aggregate Formation and Pigment-Forming Ability In order to compare the stability of the compositions comprising FVII-Tf fusion protein according to the type of a bulking agent, the lyophilized compositions of Examples 1 and 2 and Comparative Examples 1 and 2 were dissolved in 0.5 ml of distilled water, and the high molecular weight aggregate (HMW aggregate) formed during lyophilization was analyzed by GP-HPLC. For the GP-HPLC analysis, Waters Protein Pak 300 SW (7.5×300 mm, 10 μm) column was used; 50 mM sodium phosphate (pH 7.0) containing 300 mM sodium chloride was used as a mobile phase; and the resultant was detected at the flow rate of 0.5 ml/min at 215 nm wavelength. The content of the aggregate was represented as a percentage of the initial amount of FVII in the composition, and the aggregates were recovered in the forms of a dimer, an oligomer, and a multimer of the factor VII.

In addition, in order to assess the activity change of FVII fusion protein according to the type of a bulking agent, the activities of FVII fusion proteins with regard to the lyophilized compositions of Example 2 and Comparative Example 2 were measured using COASET test kit (Chromogenix, #821900-63) by chromogenic assay.

The analysis results of the amount of high molecular weight aggregate and pigment-forming ability are shown in Tables 3 and 4 below.

TABLE 3

| | Amount of high molecular weight aggregate formed during lyophilization process (%) |
|---|---|
| Example 1 | 1.43 |
| Example 2 | 0.83 |

TABLE 3-continued

| | Amount of high molecular weight aggregate formed during lyophilization process (%) |
|---|---|
| Comparative Example 1 | 3.19 |
| Comparative Example 2 | 2.09 |

TABLE 4

| | Post-lyophilization activity (%) |
|---|---|
| Example 2 | 76 |
| Comparative Example 2 | 69 |

As shown in Table 3, it was found that the compositions of Examples 1 and 2 comprising glycine as a bulking agent showed small amount of aggregate formation during lyophilization process, whereas the compositions of Comparative Examples 1 and 2 comprising mannitol as a bulking agent showed relatively large amount of aggregate formation. Also, as shown in Table 4, it was found that the composition of Example 2 showed higher post-lyophilization activity than the composition of Comparative Example 2.

These results indicate that the use of glycine as a bulking agent is effective in terms of the stability of the FVII-Tf fusion protein.

<1-2> Analysis of Storage Stability at Room Temperature

With regard to the compositions of Example 3 and Comparative Example 3, the storage stabilities at room temperature were compared by measuring the glass transition temperatures (Tg').

The glass transition temperature is a good parameter for evaluating the storage stabilities at room temperature. As the glass transition temperature is higher, the formulation is determined to be the more stable formulation.

The glass transition temperature was measured by differential scanning calorimetry (DSC) analysis. As for the measuring device, Pyris Diamond DSC having an intercooler was used. The lyophilized samples of Example 3 and Comparative Example 3 were put into aluminum pans, and were cooled to 0° C. Then, the samples were heated up to 100° C. at 5° C./min ramp rate, and the heat flow during the above process was recorded. From the record, signals including glass transition temperature (Tg') were observed. The measured glass transition temperatures (Tg') are shown in Table 5 below.

Also, the lyophilized compositions of Example 3 and Comparative Example 3 were stored for 6 months at 40° C., and then the chromogenic activities of the FVII fusion proteins were analyzed as described in Experimental Example <1-1>. The activity change ratios (%) (increase or decrease) of the FVII fusion proteins were assessed compared to those before storage. The analysis results are shown in Table 5.

TABLE 5

| | Glass transition temperature (Tg') | Change ratio of activity after storage |
|---|---|---|
| Example 3 | ≥44° C. | −6.1% |
| Comparative Example 3 | 35° C. | −77.8% |

As shown in Table 5, the composition of Example 3 comprising glycine as a bulking agent showed higher glass transition temperature than the composition of Comparative Example 3 comprising mannitol as a bulking agent. Also, the composition of Comparative Example 3 showed an activity decrease of no less than 77.8% after storage for 6 months at 40° C., whereas the composition of Example 3 showed an activity decrease of no more than 6.1%.

These results indicate that the use of glycine as a bulking agent is effective in terms of the stability of the FVII-Tf fusion protein.

<1-3> Comparison of Compositions Comprising Mannitol or Trehalose as a Bulking Agent With regard to the composition of Example 4 comprising trehalose as a bulking agent, the high molecular aggregate contents and storage stability at room temperature were compared. The analysis results are shown in Table 6.

TABLE 6

| | Amount of high molecular weight aggregate formed during lyophilization process (%) | Change ratio of the amount of high molecular weight aggregate after storage (%) | Change ratio of activity after storage (%) |
|---|---|---|---|
| Example 4 | 0.5% | −0.8% | −7.9% |
| Comparative Example 4 | 1.0% | −4.8% | −43.7% |

As shown in the above Table, it was found that the amount of high molecular weight aggregate formed during lyophilization process, the change ratio of the amount of the aggregate, and the activity after storage for 6 months at 40° C. were low in the composition of Example 4 comprising trehalose as a bulking agent, whereas the change ratio of the amount of the aggregate and the activity after storage for 6 months at 40° C. were very high in the composition of Comparative Example 4 comprising mannitol as a bulking agent.

These results indicate that the use of trehalose as a bulking agent is effective in terms of the stability of the FVII-Tf fusion protein.

Examples 5 and 6, and Comparative Example 5: Preparation of Liquid Composition with Different Types of Surfactants According to the compositions of Table 7 below, the liquid compositions (pH 8) comprising FVII-Tf fusion protein were prepared by adding various surfactants to the FVII-Tf fusion proteins obtained in Preparation Example 1.

TABLE 7

| | Ingredients | Example 5 | Example 6 | Comparative Example 5 |
|---|---|---|---|---|
| Active ingredient | FVII-Tf (mg/ml) | 1 | 1 | 1 |
| Surfactant | Poloxamer 188 (%) | 0.1 | — | — |
| | Polysorbate 20 (%) | — | 0.01 | — |
| | Polysorbate 80 (%) | — | — | 0.1 |
| Buffer | Tris (mM) | 20 | 20 | 20 |
| Stabilizer | Sodium chloride (M) | 1 | 1 | 1 |
| | Calcium chloride (mM) | 5 | 5 | 5 |
| | pH | 8 | 8 | 8 |

Experimental Example 2: Analysis of Stability of Liquid Compositions According to Type of Surfactant With regard to the liquid compositions of Examples 5 and 6 and Comparative Example 5, the suppression capability on the high molecular weight aggregate formation was measured by measuring the amount of the high molecular weight aggregate formation under the shear stress condition. Particularly, the liquid compositions were subjected to a shear stress by stirring them at a constant rate for 4 hr at room temperature. Then, the amount of high molecular weight aggregates was measured by HPLC, and the levels of increase of the high molecular weight aggregates as compared to those which were left without stirring were compared. The comparative analysis result is shown in FIG. 2.

Figure 2:
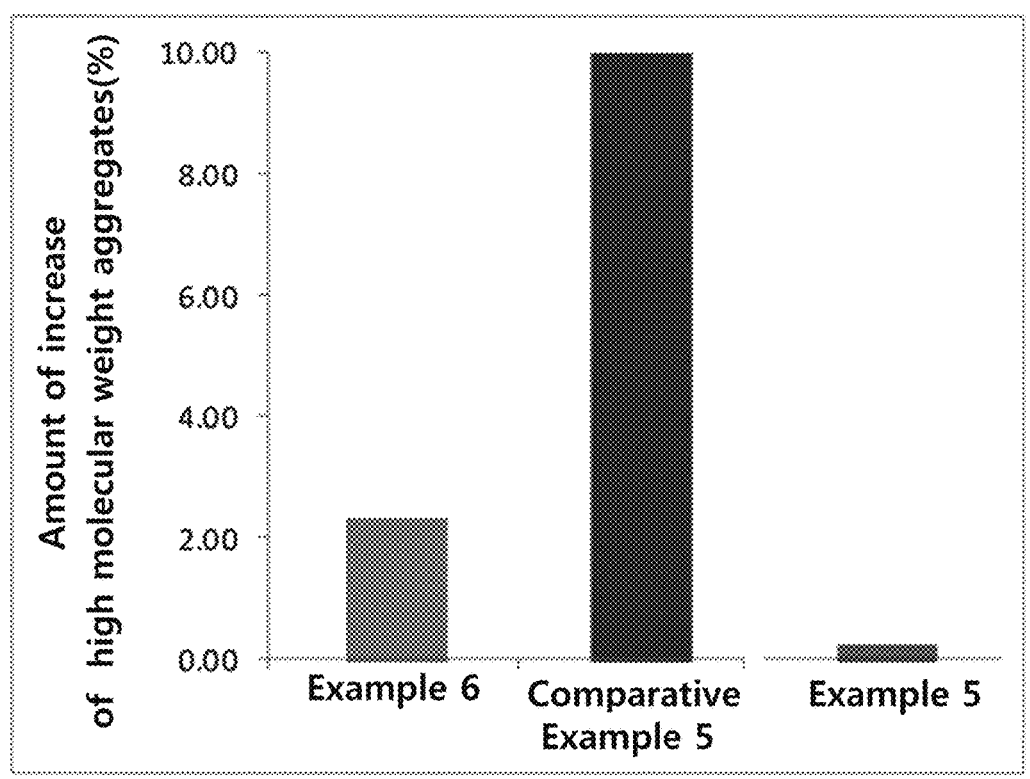
FIG. 2 is a graph showing the result of measuring the amount of increase (%) of high molecular weight aggregates formed under the shear stress conditions, with regard to liquid compositions of Examples 5 and 6, and Comparative Example 5.

As shown in FIG. 2, Comparative Example 5 comprising polysorbate 80 did not show sufficient suppression on the high molecular weight aggregate formation, whereas the compositions of Examples 5 and 6 comprising poloxamer 188 or polysorbate 20, showed high level of suppression of high molecular weight aggregates. Specifically, the composition of Examples 5 comprising poloxamer 188, showed almost complete suppression on the high molecular weight aggregate formation.

These results indicate that the use poloxamer 188 or polysorbate 20 as a surfactant is preferable in terms of the stability of the FVII-Tf fusion protein.

Examples 7 to 13: Preparation of Lyophilized Compositions in Which Bulking Agent and Surfactant are Combined According to the compositions in Table 8 below, lyophilized compositions comprising FVII-Tf fusion protein were prepared by combining glycine or trehalose as a bulking agent, with poloxamer 188 or polysorbate 20 as a surfactant.

Comparative Examples 6 and 7: Preparation of Lyophilized Compositions in Which Mannitol and Surfactant are Combined According to the compositions of Table 9 below, Comparative Examples 6 and 7 which comprise mannitol as a bulking agent and poloxamer 188 as a surfactant were prepared.

TABLE 9

| | Ingredient | Comparative Example 6 | Comparative Example 7 |
|---|---|---|---|
| Active ingredient | FVII-Tf (mg/ml) | 1 | 1 |
| Bulking agent | Mannitol (%) | 2.5 | 2.5 |
| Surfactant | Poloxamer 188 (%) | 0.1 | 0.1 |
| Buffer | L-histidine(mM) | 10 | 10 |
| Stabilizer | Sodium chloride (%) | 0.23 | 0.5 |
| | Calcium chloride (%) | 0.1 | 0.1 |
| | Trehalose (%) | 1 | 1 |
| Anti-oxidant | Methionine (%) | 0.05 | 0.05 |
| | pH | 7 | 7 |

Experimental Example 3: Stability Analysis of Lyophilized Compositions According to the Combination of Bulking Agent and Surfactant With regard to the lyophilized compositions of Examples 7, 8 and 10 to 13, and Comparative Examples 6 and 7, stability during storage was analyzed. Particularly, while storing each of the lyophilized compositions for 3 months at 25° C. and 40° C., the change ratios of the amounts of high molecular weight aggregates and the change ratios of FVII-Tf fusion protein activity were measured every month. The results are shown in Table 10 below.

TABLE 8

| | Ingredients | Example 7 | Example 8 | Example 9 | Example 10 | Example 11 | Example 12 | Example 13 |
|---|---|---|---|---|---|---|---|---|
| Active ingredient | FVII-Tf (mg/ml) | 1 | 1 | 1 | 1 | 1 | 1 | 1 |
| Bulking agent | Glycine (%) | 2.5 | 2.5 | — | — | — | — | — |
| | Trehalose (%) | — | — | 6 | 6 | 6 | 3 | 6 |
| Surfactant | Poloxamer 188 (%) | 0.1 | — | 0.1 | 0.1 | 0.1 | 0.1 | — |
| | Polysorbate 20 (%) | — | 0.01 | — | — | — | — | 0.01 |
| Buffer | L-histidine (mM) | 10 | 10 | 10 | 10 | 10 | 10 | 10 |
| Stabilizer | Sodium chloride (%) | 0.1 | 0.1 | 0.23 | 0.23 | 0.1 | 0.23 | 0.23 |
| | Calcium chloride (%) | 0.1 | 0.1 | 0.1 | 0.1 | 0.1 | 0.1 | 0.1 |
| | Trehalose (%) | 1 | 1 | — | — | — | — | — |
| | Sucrose (%) | — | 1 | — | — | — | — | — |
| | Threonine (%) | — | — | — | — | — | 2 | — |
| Anti-oxidant | Methionine (%) | 0.05 | 0.05 | 0.05 | 0.05 | 0.05 | 0.02 | 0.05 |
| | pH | 7 | 7 | 7 | 6.5 | 7 | 7 | 7 |

TABLE 10

| | Storage Stability | 1 month of storage | | 2 months of storage | | 3 months of storage | |
|---|---|---|---|---|---|---|---|
| | | 25° C. | 40° C. | 25° C. | 40° C. | 25° C. | 40° C. |
| Example 7 | Change ratio of high molecular weight aggregate (%) | 0.7 | 0.7 | 0.7 | 0.8 | 0.6 | 0.6 |
| | Change ratio of activity (%) | −6.9 | −2.2 | 1.0 | 3.7 | 3.7 | −0.9 |
| Example 8 | Change ratio of high molecular weight aggregate (%) | 0.2 | 0.2 | 0.3 | 0.4 | 0.1 | 0.2 |
| | Change ratio of activity (%) | Not measured | Not measured | Not measured | Not measured | −2.4 | 5.0 |
| Example 10 | Change ratio of high molecular weight aggregate (%) | 0.6 | 0.4 | 0.4 | 0.3 | 0.2 | 0.2 |
| | Change ratio of activity (%) | Not measured | Not measured | −3.1 | 1.5 | Not measured | Not measured |
| Example 11 | Change ratio of high molecular weight aggregate (%) | 0.5 | 0.5 | 0.4 | 0.4 | 0.3 | 0.3 |
| | Change ratio of activity (%) | −3.6 | 0.6 | 6.0 | 3.7 | 3.2 | −8.1 |
| Example 12 | Change ratio of high molecular weight aggregate (%) | 0.3 | 0.5 | 0.3 | 0.5 | 0.3 | 0.4 |
| | Change ratio of activity (%) | −2.0 | −1.2 | −0.5 | 1.9 | 7.7 | 5.0 |
| Example 13 | Change ratio of high molecular weight aggregate (%) | 0.0 | 0.0 | 0.1 | 0.1 | 0.2 | 0.0 |
| | Change ratio of activity (%) | 3.2 | −2.0 | 7.2 | 3.1 | 4.8 | −0.2 |
| Comparative Example 6 | Change ratio of high molecular weight aggregate (%) | 0.3 | 0.4 | 0.3 | 0.5 | 0.2 | 0.5 |
| | Change ratio of activity (%) | −6.8 | −14.6 | −12.9 | −14.6 | −5.4 | −32.2 |
| Comparative Example 7 | Change ratio of high molecular weight aggregate (%) | 0.2 | 0.5 | 0.1 | 1.5 | 0.1 | 2.5 |
| | Change ratio of activity (%) | 5.8 | −35.2 | 6.3 | −44.8 | 9.8 | −58.3 |

As shown in Table 10, it was found that the change ratios of the amount of aggregates and the change ratios of the activity were low in the compositions comprising glycine or trehalose as a bulking agent, and poloxamer 188 or polysorbate 20 as a surfactant, whereas those were high in the compositions of Comparative Examples 6 and 7 comprising other bulking agents and surfactants.

These results indicate that excellent storage stability can be achieved by combining glycine or trehalose as a bulking agent, with poloxamer 188 or polysorbate 20 as a surfactant.

What is claimed is:

1. A pharmaceutical composition, comprising:
   a fusion protein comprising Factor VII and transferrin, wherein the transferrin is a protein having at least 95% sequence identity to SEQ ID NO:2 and is linked to the C-terminus of the Factor VII; trehalose or glycine; and a pharmaceutically acceptable carrier.

2. The pharmaceutical composition of claim 1, further comprising a surfactant selected from polysorbate 20 or poloxamer 188.

3. The pharmaceutical composition of claim 1, further comprising at least one stabilizer selected from the group consisting of sodium chloride, calcium chloride, trehalose, sucrose and threonine.

4. The pharmaceutical composition of claim 1, further comprising L-histidine or methionine.

5. The pharmaceutical composition of claim 1, wherein the fusion protein comprises a restriction enzyme recognition sequence between the C-terminus of the Factor VII and the transferrin.

6. The pharmaceutical composition of claim 1, wherein the fusion protein comprises a linker between the Factor VII and the transferrin.

7. The pharmaceutical composition of claim 1, which does not comprise a polyol.

8. The pharmaceutical composition of claim 7, wherein the polyol is mannitol.

9. The pharmaceutical composition of claim 1, which does not comprise glycylglycine.

10. The pharmaceutical composition of claim 1, wherein the trehalose or glycine is comprised in an amount of 0.1 to 20 weight % based on the total weight of the composition.

11. The pharmaceutical composition of claim 2, wherein the polysorbate 20 or the poloxamer 188 is comprised in an amount of 0.0005 to 2.5 weight % or 0.05 to 2.5 weight % based on the total weight of the composition, respectively.

12. The pharmaceutical composition of claim 1, further comprising:
   a surfactant selected from polysorbate 20 and poloxamer 188;
   a stabilizer selected from the group consisting of sodium chloride, calcium chloride, trehalose, sucrose, and threonine; and
   L-histidine or methionine.

13. The pharmaceutical composition of claim 12, which comprises 0.1 to 20 weight % of trehalose or glycine, and 0.0005 to 2.5 weight % of polysorbate 20 or poloxamer 188, based on the total weight of the composition, respectively.

14. The pharmaceutical composition of claim 13, which comprises 0.05 to 2.5 weight % of polysorbate 20 or poloxamer 188, based on the total weight of the composition.

15. The pharmaceutical composition of claim 12, wherein the fusion protein comprises a restriction enzyme recognition sequence between the C-terminus of the Factor VII and the transferrin, and
   wherein the fusion protein comprises a linker between the Factor VII and the transferrin.

16. The pharmaceutical composition of claim 12, which does not comprise a polyol.

* * * * *

SEQUENCE LISTING

<160> NUMBER OF SEQ ID NOS: 24

<210> SEQ ID NO 1
<211> LENGTH: 444
<212> TYPE: PRT
<213> ORGANISM: Homo sapiens

<400> SEQUENCE: 1

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

```
Leu His Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
 50                  55                  60

Ala Arg Glu Ile Phe Lys Asp Ala Glu Arg Thr Lys Leu Phe Trp Ile
 65                  70                  75                  80

Ser Tyr Ser Asp Gly Asp Gln Cys Ala Ser Ser Pro Cys Gln Asn Gly
                     85                  90                  95

Gly Ser Cys Lys Asp Gln Leu Gln Ser Tyr Ile Cys Phe Cys Leu Pro
                100                 105                 110

Ala Phe Glu Gly Arg Asn Cys Glu Thr His Lys Asp Asp Gln Leu Ile
                115                 120                 125

Cys Val Asn Glu Asn Gly Gly Cys Glu Gln Tyr Cys Ser Asp His Thr
            130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
                180                 185                 190

Gly Gly Lys Val Cys Pro Lys Gly Glu Cys Pro Trp Gln Val Leu Leu
                195                 200                 205

Leu Val Asn Gly Ala Gln Leu Cys Gly Gly Thr Leu Ile Asn Thr Ile
            210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
                260                 265                 270

Val Pro Gly Thr Thr Asn His Asp Ile Ala Leu Leu Arg Leu His Gln
            275                 280                 285

Pro Val Val Leu Thr Asp His Val Val Pro Leu Cys Leu Pro Glu Arg
            290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Lys Gly Asp Ser Gly Gly
            370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
                420                 425                 430

Pro Arg Pro Gly Val Leu Leu Arg Ala Pro Phe Pro
            435                 440
```

<210> SEQ ID NO 2
<211> LENGTH: 679
<212> TYPE: PRT
<213> ORGANISM: Homo sapiens

<400> SEQUENCE: 2

```
Val Pro Asp Lys Thr Val Arg Trp Cys Ala Val Ser Glu His Glu Ala
1               5                   10                  15

Thr Lys Cys Gln Ser Phe Arg Asp His Met Lys Ser Val Ile Pro Ser
            20                  25                  30

Asp Gly Pro Ser Val Ala Cys Val Lys Lys Ala Ser Tyr Leu Asp Cys
        35                  40                  45

Ile Arg Ala Ile Ala Ala Asn Glu Ala Asp Ala Val Thr Leu Asp Ala
50                  55                  60

Gly Leu Val Tyr Asp Ala Tyr Leu Ala Pro Asn Asn Leu Lys Pro Val
65                  70                  75                  80

Val Ala Glu Phe Tyr Gly Ser Lys Glu Asp Pro Gln Thr Phe Tyr Tyr
                85                  90                  95

Ala Val Ala Val Val Lys Lys Asp Ser Gly Phe Gln Met Asn Gln Leu
            100                 105                 110

Arg Gly Lys Lys Ser Cys His Thr Gly Leu Gly Arg Ser Ala Gly Trp
        115                 120                 125

Asn Ile Pro Ile Gly Leu Leu Tyr Cys Asp Leu Pro Glu Pro Arg Lys
130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
                165                 170                 175

Cys Gly Cys Ser Thr Leu Asn Gln Tyr Phe Gly Tyr Ser Gly Ala Phe
            180                 185                 190

Lys Cys Leu Lys Asp Gly Ala Gly Asp Val Ala Phe Val Lys His Ser
        195                 200                 205

Thr Ile Phe Glu Asn Leu Ala Asn Lys Ala Asp Arg Asp Gln Tyr Glu
210                 215                 220

Leu Leu Cys Leu Asp Asn Thr Arg Lys Pro Val Asp Glu Tyr Lys Asp
225                 230                 235                 240

Cys His Leu Ala Gln Val Pro Ser His Thr Val Val Ala Arg Ser Met
                245                 250                 255

Gly Gly Lys Glu Asp Leu Ile Trp Glu Leu Leu Asn Gln Ala Gln Glu
            260                 265                 270

His Phe Gly Lys Asp Lys Ser Lys Glu Phe Gln Leu Phe Ser Ser Pro
        275                 280                 285

His Gly Lys Asp Leu Leu Phe Lys Asp Ser Ala His Gly Phe Leu Lys
290                 295                 300

Val Pro Pro Arg Met Asp Ala Lys Met Tyr Leu Gly Tyr Glu Tyr Val
305                 310                 315                 320

Thr Ala Ile Arg Asn Leu Arg Glu Gly Thr Cys Pro Glu Ala Pro Thr
                325                 330                 335

Asp Glu Cys Lys Pro Val Lys Trp Cys Ala Leu Ser His His Glu Arg
            340                 345                 350

Leu Lys Cys Asp Glu Trp Ser Val Asn Ser Val Gly Lys Ile Glu Cys
        355                 360                 365

Val Ser Ala Glu Thr Thr Glu Asp Cys Ile Ala Lys Ile Met Asn Gly
370                 375                 380
```

Glu Ala Asp Ala Met Ser Leu Asp Gly Gly Phe Val Tyr Ile Ala Gly
385                 390                 395                 400

Lys Cys Gly Leu Val Pro Val Leu Ala Glu Asn Tyr Asn Lys Ser Asp
            405                 410                 415

Asn Cys Glu Asp Thr Pro Glu Ala Gly Tyr Phe Ala Val Ala Val Val
        420                 425                 430

Lys Lys Ser Ala Ser Asp Leu Thr Trp Asp Asn Leu Lys Gly Lys Lys
    435                 440                 445

Ser Cys His Thr Ala Val Gly Arg Thr Ala Gly Trp Asn Ile Pro Met
450                 455                 460

Gly Leu Leu Tyr Asn Lys Ile Asn His Cys Arg Phe Asp Glu Phe Phe
465                 470                 475                 480

Ser Glu Gly Cys Ala Pro Gly Ser Lys Lys Asp Ser Ser Leu Cys Lys
            485                 490                 495

Leu Cys Met Gly Ser Gly Leu Asn Leu Cys Glu Pro Asn Asn Lys Glu
        500                 505                 510

Gly Tyr Tyr Gly Tyr Thr Gly Ala Phe Arg Cys Leu Val Glu Lys Gly
    515                 520                 525

Asp Val Ala Phe Val Lys His Gln Thr Val Pro Gln Asn Thr Gly Gly
530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Glu Tyr Ala Asn
            565                 570                 575

Cys His Leu Ala Arg Ala Pro Asn His Ala Val Val Thr Arg Lys Asp
        580                 585                 590

Lys Glu Ala Cys Val His Lys Ile Leu Arg Gln Gln Gln His Leu Phe
    595                 600                 605

Gly Ser Asn Val Thr Asp Cys Ser Gly Asn Phe Cys Leu Phe Arg Ser
610                 615                 620

Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Glu Tyr Val
            645                 650                 655

Lys Ala Val Gly Asn Leu Arg Lys Cys Ser Thr Ser Ser Leu Leu Glu
        660                 665                 670

Ala Cys Thr Phe Arg Arg Pro
        675

<210> SEQ ID NO 3
<211> LENGTH: 25
<212> TYPE: DNA
<213> ORGANISM: Artificial Sequence
<220> FEATURE:
<223> OTHER INFORMATION: FVII-F primer

<400> SEQUENCE: 3
aggggcagca ctgcagagat ttcat                                    25

<210> SEQ ID NO 4
<211> LENGTH: 25
<212> TYPE: DNA
<213> ORGANISM: Artificial Sequence
<220> FEATURE:
<223> OTHER INFORMATION: FVII-R primer

<400> SEQUENCE: 4
tatgggattt ggtgccagga cagtt                                          25

<210> SEQ ID NO 5
<211> LENGTH: 5
<212> TYPE: PRT
<213> ORGANISM: Artificial Sequence
<220> FEATURE:
<223> OTHER INFORMATION: 5 amino acid linker

<400> SEQUENCE: 5

Gly Gly Gly Gly Ser
1               5

<210> SEQ ID NO 6
<211> LENGTH: 10
<212> TYPE: PRT
<213> ORGANISM: Artifical Sequence
<220> FEATURE:
<223> OTHER INFORMATION: 10 amino acid linker

<400> SEQUENCE: 6

Gly Gly Gly Gly Ser Gly Gly Gly Gly Ser
1               5                   10

<210> SEQ ID NO 7
<211> LENGTH: 15
<212> TYPE: PRT
<213> ORGANISM: Artificial sequence
<220> FEATURE:
<223> OTHER INFORMATION: 15 amino acid linker

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 20
<212> TYPE: PRT
<213> ORGANISM: Artificial Sequence
<220> FEATURE:
<223> OTHER INFORMATION: 20 amino acid linker

<400> SEQUENCE: 8

Gly Gly Gly Gly Ser Gly Gly Gly Gly Ser Gly Gly Gly Gly Ser Gly
1               5                   10                  15

Gly Gly Gly Ser
            20

<210> SEQ ID NO 9
<211> LENGTH: 25
<212> TYPE: PRT
<213> ORGANISM: Artificial Sequence
<220> FEATURE:
<223> OTHER INFORMATION: 25 amino acid linker

<400> SEQUENCE: 9

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 10
<211> LENGTH: 30
<212> TYPE: PRT
<213> ORGANISM: Artificial Sequence

```
<220> FEATURE:
<223> OTHER INFORMATION: 30 amino acid linker

<400> SEQUENCE: 10

Gly Gly Gly Gly Ser Gly Gly Gly Gly Ser Gly Gly Gly Gly Ser Gly
1               5                   10                  15

Gly Gly Gly Ser Gly Gly Gly Ser Gly Gly Gly Ser
            20                  25              30

<210> SEQ ID NO 11
<211> LENGTH: 35
<212> TYPE: PRT
<213> ORGANISM: Artificial Sequence
<220> FEATURE:
<223> OTHER INFORMATION: 35 amino acid linker

<400> SEQUENCE: 11

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 12
<211> LENGTH: 40
<212> TYPE: PRT
<213> ORGANISM: Artificial Sequence
<220> FEATURE:
<223> OTHER INFORMATION: 40 amino acid linker

<400> SEQUENCE: 12

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 13
<211> LENGTH: 45
<212> TYPE: PRT
<213> ORGANISM: Artificial Sequence
<220> FEATURE:
<223> OTHER INFORMATION: 45 amino acid linker

<400> SEQUENCE: 13

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 14
<211> LENGTH: 50
<212> TYPE: PRT
<213> ORGANISM: Artificial Sequence
<220> FEATURE:
<223> OTHER INFORMATION: 50 amino acid linker

<400> SEQUENCE: 14

Gly Gly Gly Gly Ser Gly Gly Gly Gly Ser Gly Gly Gly Gly Ser Gly
```

```
                1               5                   10                  15
Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
        35                  40                  45

Gly Ser
    50

<210> SEQ ID NO 15
<211> LENGTH: 55
<212> TYPE: PRT
<213> ORGANISM: Artificial Sequence
<220> FEATURE:
<223> OTHER INFORMATION: 55 amino acid linker

<400> SEQUENCE: 15

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
        35                  40                  45

Gly Ser Gly Gly Gly Gly Ser
    50                  55

<210> SEQ ID NO 16
<211> LENGTH: 60
<212> TYPE: PRT
<213> ORGANISM: Artificial Sequence
<220> FEATURE:
<223> OTHER INFORMATION: 60 amino acid linker

<400> SEQUENCE: 16

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser
    50                  55                  60

<210> SEQ ID NO 17
<211> LENGTH: 65
<212> TYPE: PRT
<213> ORGANISM: Artificial Sequence
<220> FEATURE:
<223> OTHER INFORMATION: 65 amino acid linker

<400> SEQUENCE: 17

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser
65
```

```
<210> SEQ ID NO 18
<211> LENGTH: 70
<212> TYPE: PRT
<213> ORGANISM: Artificial Sequence
<220> FEATURE:
<223> OTHER INFORMATION: 70 amino acid linker

<400> SEQUENCE: 18

Gly Gly Gly Gly Ser Gly Gly Gly Ser Gly Gly Gly Gly Ser Gly
1               5                   10                  15

Gly Gly Ser Gly Gly Gly Gly Ser Gly Gly Gly Ser Gly Gly
            20                  25                  30

Gly Gly Ser Gly Gly Gly Gly Ser Gly Gly Gly Ser Gly Gly Gly
            35                  40                  45

Gly Ser Gly Gly Gly Gly Ser Gly Gly Gly Ser Gly Gly Gly Gly
    50                  55                  60

Ser Gly Gly Gly Gly Ser
65                  70

<210> SEQ ID NO 19
<211> LENGTH: 75
<212> TYPE: PRT
<213> ORGANISM: Artificial Sequence
<220> FEATURE:
<223> OTHER INFORMATION: 75 amino acid linker

<400> SEQUENCE: 19

Gly Gly Gly Gly Ser Gly Gly Gly Ser Gly Gly Gly Gly Ser Gly
1               5                   10                  15

Gly Gly Ser Gly Gly Gly Gly Ser Gly Gly Gly Ser Gly Gly
            20                  25                  30

Gly Gly Ser Gly Gly Gly Gly Ser Gly Gly Gly Ser Gly Gly Gly
            35                  40                  45

Gly Ser Gly Gly Gly Gly Ser Gly Gly Gly Ser Gly Gly Gly Gly
    50                  55                  60

Ser Gly Gly Gly Gly Ser Gly Gly Gly Gly Ser
65                  70                  75

<210> SEQ ID NO 20
<211> LENGTH: 80
<212> TYPE: PRT
<213> ORGANISM: Artificial Sequence
<220> FEATURE:
<223> OTHER INFORMATION: 80 amino acid linker

<400> SEQUENCE: 20

Gly Gly Gly Gly Ser Gly Gly Gly Ser Gly Gly Gly Gly Ser Gly
1               5                   10                  15

Gly Gly Ser Gly Gly Gly Gly Ser Gly Gly Gly Ser Gly Gly Gly
            20                  25                  30

Gly Gly Ser Gly Gly Gly Gly Ser Gly Gly Gly Ser Gly Gly Gly
            35                  40                  45

Gly Ser Gly Gly Gly Ser Gly Gly Gly Ser Gly Gly Gly Gly
    50                  55                  60

Ser Gly Gly Gly Gly Ser Gly Gly Gly Ser Gly Gly Gly Ser
65                  70                  75                  80

<210> SEQ ID NO 21
<211> LENGTH: 85
```

<212> TYPE: PRT
<213> ORGANISM: Artificial Sequence
<220> FEATURE:
<223> OTHER INFORMATION: 85 amino acid linker

<400> SEQUENCE: 21

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser
                85

<210> SEQ ID NO 22
<211> LENGTH: 90
<212> TYPE: PRT
<213> ORGANISM: Artificial Sequence
<220> FEATURE:
<223> OTHER INFORMATION: 90 amino acid linker

<400> SEQUENCE: 22

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser
                85                  90

<210> SEQ ID NO 23
<211> LENGTH: 95
<212> TYPE: PRT
<213> ORGANISM: Artificial Sequence
<220> FEATURE:
<223> OTHER INFORMATION: 95 amino acid linker

<400> SEQUENCE: 23

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser

```
<210> SEQ ID NO 24
<211> LENGTH: 100
<212> TYPE: PRT
<213> ORGANISM: Artificial Sequence
<220> FEATURE:
<223> OTHER INFORMATION: 100 amino acid linker

<400> SEQUENCE: 24

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100
```